United States Patent [19]

Page et al.

[11] Patent Number: 4,743,699

[45] Date of Patent: * May 10, 1988

[54] HOMOGENEOUS CATALYTIC SYSTEM AND A PROCESS FOR THE PREPARATION OF SAME

[75] Inventors: Philip R. Page, Parede; Ivan Villax, Lisboa, both of Portugal

[73] Assignee: Plurichemie Anstalt, Liechtenstein

[*] Notice: The portion of the term of this patent subsequent to Oct. 29, 2002 has been disclaimed.

[21] Appl. No.: 732,952

[22] Filed: May 13, 1985

Related U.S. Application Data

[63] Continuation-in-part of Ser. No. 458,068, Jan. 14, 1983, Pat. No. 4,550,096.

[30] Foreign Application Priority Data

Jan. 19, 1982 [PT] Portugal ................................... 74303
Dec. 30, 1982 [PT] Portugal ................................... 76061
Dec. 28, 1984 [PT] Portugal ................................... 79774

[51] Int. Cl.$^4$ ..................... C07F 15/00; C07C 103/19
[52] U.S. Cl. ........................................ 556/23; 556/13; 502/166; 260/351.5
[58] Field of Search ................... 556/13, 23; 502/166; 260/351.5

[56] References Cited

U.S. PATENT DOCUMENTS

| | | | |
|---|---|---|---|
| 3,954,862 | 5/1976 | Morris, Jr. .................. | 260/351.5 |
| 3,962,131 | 6/1977 | Faubl et al. ................. | 260/351.5 |
| 4,001,321 | 1/1977 | Faubl ........................ | 260/351.5 |
| 4,031,137 | 6/1977 | Schmitt, Jr. et al. ......... | 260/351.5 |
| 4,190,595 | 2/1980 | Diamond et al. .............. | 556/23 X |
| 4,207,258 | 6/1980 | Broggi et al. ............... | 260/351.5 |
| 4,500,458 | 2/1985 | Villar et al. ............... | 260/351.5 |
| 4,550,096 | 10/1985 | Page et al. ................. | 556/13 X |
| 4,597,904 | 7/1986 | Page ......................... | 260/351.5 |

OTHER PUBLICATIONS

Chemical Abstracts 100 22516h (1984).
Chemical Abstracts 78 97767b (1973).
Chemical Abstracts 95 214275d (1981).
Chemical Abstracts 90 104102j (1979).

*Primary Examiner*—Richard L. Raymond
*Assistant Examiner*—Raymond Covington
*Attorney, Agent, or Firm*—Ostrolenk, Faber, Gerb & Soffen

[57] ABSTRACT

A homogeneous stereospecific rhodium complex hydrogenation catalyst is prepared using a degassed organic solvent and eventually water.

14 Claims, No Drawings

HOMOGENEOUS CATALYTIC SYSTEM AND A PROCESS FOR THE PREPARATION OF SAME

This is a continuation-in-part of Application Ser. No. 458,068, filed Jan. 14, 1983, now U.S. Pat. No. 4,550,096.

Homogeneous catalysts as a general group have been known for a considerable time, starting with soluble metal salts in the early part of this century. The use of d-block transition metals with organic donor ligands, exemplified for example by Wilkinson et al. in Journal of the Chemical Society 1966, 1711–1732, paved the way to catalysts with highly specific catalytic behaviour.

The aim of this invention was to find catalysts for the hydrogenation of the exocyclic 6-methylene group of a 6-deoxy-6-demethyl-6-methylene-tetracycline, that would allow the use of minimal quantities of catalysts, whilst giving high yields and high optical purities of the $\alpha$-6-deoxy-tetracyclines. These latter compounds, especially the $\alpha$-$\not\neq$-deoxy-5-hydroxytetracycline, commonly known as doxycycline, are well-known anti-bacterial agents. One of the major problems associated with the prior art techniques for this transformation is the co-production of the $\beta$-epimers. The presence of these epimers, which are effectively devoid of clinical use, require the use of extensive purification techniques, in order that a pure product be obtained.

It will be seen from the following that the catalysts of the present invention fulfill these aims. A further detailed discussion of the use of these catalysts is given in U.S. Pat. No. 4,500,458.

The prior art for this hydrogenation process is extensive, so only the salient parts of the various published procedures will be herein reviewed.

Prior to 1972, only the use of heterogeneous catalysts was taught. Thus, in U.S. Pat. No. 3,200,149, 5% rhodium-on-carbon was used, furnishing a 24% weight/weight yield of a $\alpha$-6-deoxy-5-hydroxytetracycline from 6-deoxy-6-demethyl-6-methylene-5-hydroxytetracycline. A similar amount of the $\beta$-epimer was formed at the same time, its removal being effected by counter-current distribution.

U.S. Pat. No. 3,44,198 showed that the use of 5% palladium-on-carbon, in the presence of a catalyst poison, such as quinoline-sulphur, could improve the ratio of the $\alpha$-epimer to the $\beta$-epimer. However, the yield was still low and the requirement for extensive purification still remained.

British Pat. No. 1,360,006 then showed that the use of a mixture of hydrazine and palladium-on-carbon gave improved specificity for the required $\alpha$-epimer, but in this case the major impurity was the 6-deoxy-6-demethyl-6-methylene-5-hydroxytetracycline, when the process was started from the 11a-chloro intermediate.

A further example was provided in the West German Pat. No. 2,136,621, wherein the use of Raney Nickel is claimed.

In addition to these, various other patents appeared, such as U.S. Pat. Nos. 3,397,231, 3,795,707 and 4,061,676, which were solely aimed at new purification techniques. These processes were often long and involved, and demonstrate clearly the poor quality of the products from the then known processes.

In 1972, the first use of a homogeneous catalyst was claimed, being fully described in U.S. Pat. No. 4,207,258. The starting materials were the 11a-substituted tetracyclines and the catalyst was tris(triphenylphosphine)chlororhodium (I), along with several analogues. The examples contained therein described both higher yields and improved stereospecificity, although the content of the $\beta$-epimer was still quoted at about 5%. Additionally, the typical amount of catalyst was 0.22 parts per part of starting tetracycline.

U.S. Pat. No. 3,962,331, with a priority of 1973, effectively extended the coverage of U.S. Pat. No. 4,207,258, by including 11a-substituted tetracyclines in the allowed starting materials. However, the $\beta$-epimer was still produced in about 5%. In the case of 11a-chloro-6-deoxy-6-demethyl-6-methylene-5-hydroxytetracycline p-toluenesulphonate, about 0.003 parts of rhodium are used per part of starting material.

In 1973, French Pat. No. 2,216,268 disclosed the use of the same catalyst and the hplc analysis of the reaction mixture of a typical example showed the ratio of the $\alpha$-epimer to the $\beta$-epimer to be 92:8. In this example, the necessary catalyst contained 0.13 parts of rhodium per part of the 6-deoxy-6-demethyl-6-methylene-5-hydroxytetracycline to be hydrogenated.

In U.S. Pat. No. 3,954,862, the use of rhodium-on-carbon is described, when mixed with a tertiary phosphine and a promoter, such as hydrochloric acid. We have shown that this mixture, in the presence of a solvent, such as methanol, will produce a soluble rhodium complex, probably that claimed in the previous three patents. Typical examples showed that formation of the un-required $\beta$-epimer still occurred, in quantities from 1% to 5%. Normally, 0.1 to 0.01 parts of rhodium were employed per part of the 6-deoxy-6-demethyl-5-hydroxytetracycline. The use of 0.019 parts gave a product still containing 45% starting material, and even addition of a further 0.019 parts and continuation of the hydrogenation still left 15% starting material in the product.

U.S. Pat. No. 3,907,890 describes the use of cobalt octacarbonyl, triphenylphosphine and hydrochloric acid. Whilst this is not a hydrogenation, since no hydrogen is added "per se", the reaction gives varying amounts of the $\beta$-epimer, ranging from 17% to about 0.5%. Additionally, the stoichiometric yield varies between 54% and 72%. Overall, it can be seen that this process produces considerable variances both in yield and purity.

U.S. Pat. No. 4,001,321 uses as catalyst dicarboxylato(triphenylphosphine)rhodium (II), typically in about 0.01 parts of rhodium per part of 6-deoxy-6-demethyl-6-methylene-5-hydroxytetracycline. Again, the product is contaminated by 2–3% of the $\beta$-epimer.

Finally, U.S. Pat. No. 3,962,131 uses an unknown catalyst prepared by the action of one mole of rhodium trichloride with two moles of sodium acetate, and finally with triphenylphosphine. Unfortunately, there is no rhodium analysis on the obtained catalyst, but calculations would indicate, based in the assumption that the catalyst contains all of the rhodium present, about 0.003 parts of rhodium are required for each part of the 6-deoxy-6-demethyl-6-methylene-5-hydroxytetracycline. Again unfortunately, no chromatographic analysis was included, so the content of the $\beta$-epimer is unknown.

Thus, it can be easily seen that there is a current need for catalysts, which fulfil the following conditions:
1. Use of less than 0.001 parts per part of the tetracycline to be hydrogenated;
2. Will produce a good yield of the hydrogenated product;

3. Will not produce, or allow only negligible production of the un-required β-epimer.

Said parent U.S. patent application is Ser. No. 458,068 describes a homogeneous rhodium catalyst containing, besides a tertiary phosphine, a hydrazine as a ligand. The incorporation of a hydrazine as a ligand into the complex has the unexpected result of improving the regio-specificity and stereo-specificity of the catalyst for the hydrogenation of exocyclic methylene groups, such as for instance in the hydrogenation of methacycline to alpha-6-deoxy-oxytetracycline. A significant reduction in the amount of catalyst employed in relation to the substrate, as well as a reduction of the pressure and reaction time are achieved. The process described therein has been found not to allow attainment of catalyst in a completely pure form, i.e. the catalyst is contaminated by oxygen absorbed during their preparation. The present invention effectively overcomes this problem, by careful control of the reaction conditions, so that it is possible to obtain complexes each with a uniform and well defined composition.

According to the invention, there is provided a compound useful as a homogeneous hydrogenation catalyst, which compound consists of the product of the reaction of rhodium trichloride or tris(triphenylphosphine)-chlororhodium (I), with a hydrazine or a salt thereof.

The catalysts of the present invention offer great advantages not only in the field of tetracyclines, but also in other fields where stereospecific homogeneous catalysts is required.

U.S. Pat. No. 3,463,830 describes the preparation of zero valent platinum and palladium catalysts, by the reduction of these metals from oxidation state II by the use of the reducing agent, hydrazine. The function of the hydrazine is merely as a reducing agent, and it is not incorporated into the catalyst so prepared. As will be described hereinbelow, the compounds of the present invention differ from those of the U.S. Pat. No. 3,463,830 in that the hydrazine is incorporated into the rhodium complex as a ligand and surprisingly the rhodium is not reduced to the zero valency state.

U.S. Pat. No. 3,956,177 describes compositions useful as hydroformylation catalysts, prepared by contacting an organorhodium halide with a hydrazine and a phosphorus-containing adjuvant, to form an intimate mixture thereof. These catalysts are not apparently compounds and are not described as useful for the hydrogenation of carbon/carbon double bonds, but as catalysts for hydroformylation reactions.

Certain of the catalysts of the present invention have been structurally analysed by X-ray crystallography and shown to have novel structures. In other cases, where the crystals were not large enough for such a study, other analytical techniques have been used, in order that their novelty could be established without question.

The catalysts of the present invention can be prepared by reacting tris(triphenylphosphine)chlororhodium (I) or rhodium trichloride with a hydrazine or a salt thereof, both eventually in the presence of a tertiary phosphine.

In the first case, the hydrazine to be reacted with the tris(triphenylphosphine)chlororhodium (I) has the general structure $R'_1R'_2N.NR'_3R'_4$, wherein $R'_1$, $R'_2$, $R'_3$ and $R'_4$ are lower alkyl groups or hydrogen, with the proviso that when $R'_1$ is a phenyl or benzenesulphonyl group, then $R'_2$, $R'_3$ and $R'_4$ can only be hydrogen. A preferred hydrazine is hydrazine itself, preferably in the form of the hydrate.

The hydrazine is normally present in an excess based upon the number of moles of rhodium present, this excess being understood to mean from slightly above equimolar to a hundred-fold molar excess. It is preferred that 3 moles of the hydrazine are used for each mole of rhodium, although a 50 mole/mole excess gives equally useful catalysts.

The preparation can be carried out in the presence or absence of triphenylphosphine. The addition of such a compound to the reaction finds its basis in the teachings of U.S. Pat. No. 3,463,830, wherein complexes of palladium and platinum with tertiary phosphines are reduced in the presence of hydrazine and excess tertiary phosphine to the zero valent palladium and platinum tertiary phosphine complexes. It is also stated in the same patent that omission of the excess tertiary phosphine from the reaction leads to the preparation of co-ordinatively unsaturated zero valent palladium and platinum tertiary phosphine complexes. The function of the hydrazine is merely as a reducing agent, and it is not incorporated into the catalyst so prepared. Included in the present invention is the preparation of the novel catalysts, either in the presence or absence of triphenylphosphine, which can be present in up to 20 moles per mole of rhodium present in the reaction. Typically, between 3 and 15 moles/mole are preferred. It is to be noted that contrary to the teaching in U.S. Pat. No. 3,463,830, the hydrazine is incorporated into the product, whilst surprisingly reduction of the rhodium to the zero valent state is not observed.

The reaction medium can be chosen from a lower alcohol, which is also intended to encompass glycols, and cyclic ethers. Typical of the preferred solvents are methanol, ethanol, propanol, propan-2-ol, butanol, 2-methyl-propan-2-ol, ethan-1,2-diol and tetrahydrofuran, with methanol, ethanol, propan-2-ol and butanol being especially preferred.

The reaction is carried out between 0° C. and 100° C., with the preferred temperature between room temperature and about 90° C. Typically, the reaction can be carried out at room temperature, although as would be expected, it proceeds faster with elevated temperatures. The reaction can be followed visually in that the initial colour of the reaction mixture is purple and that of the catalysts of the present invention is usually between yellow and brown, including orange. Thus, the time for the reaction, which is dependant on the temperature, can be judged quite easily. It is typically between a few minutes and two hours. Whilst the catalysts can be prepared as described above, the use of an inert atmosphere, such as nitrogen, is preferred.

When the reaction is judged complete, the catalysts can be obtained by conventional means well known to those skilled in the art. Normally, the addition of a miscible organic solvent, in which the catalysts are insoluble, and with which the catalysts do not react, followed by filtration and washing with the same organic solvent, is the method of choice. The preferred organic solvent is di-isopropyl ether. It might be found in some instances, that a catalyst of the present invention is insoluble in the reaction mixture, in which case it can be obtained by simple filtration and washing. The catalysts are then dried at room temperature.

A further inventive feature of the present invention is that the catalysts can be prepared and used without actually isolating them. Thus, one mixes the tris(triphenylphosphine)chlororhodium (I) with a hydrazine in a suitable solvent, eventually with the presence of triphenyl phosphine, stirs at the required temperature until the colour change indicates complete reaction. Then, the 6-deoxy-6-demethyl-6-methylene-5-hydroxytetracycline or the 11a-halo analogue is added, together with more solvent and more triphenyl phosphine as required. This mixture is then hydrogenated in the normal fashion to obtain the required product. This process is more fully described in U.S. Pat. No. 4,500,458.

As previously indicated, the catalysts can be prepared from rhodium trichloride, a hydrazine, or a salt thereof, and triphenyl phosphine in a suitable solvent mixture. The rhodium trichloride is preferably in the form of its trihydrate. The hydrazine has a general formula of $R'_1R'_2N \cdot NR'_3R'_4$, wherein $R'_1$, $R'_2$, $R'_3$ and $R'_4$ are as previously defined, and is preferably hydrazine itself, phenylhydrazine, benzenesulphonylhydrazine, N,N-dimethylhydrazine, N,N'-dimethylhydrazine and tetramethylhydrazine, and salts thereof. Particularly preferred are hydrazine hydrate and hydrazine dihydrochloride.

The hydrazine is generally present in an excess based upon the quantity of rhodium in the reaction, typically but not exclusively about 10 moles/mole of rhodium.

Typically, the triphenyl phosphine is present in excess with respect to the molar quantity of rhodium present, the range of between 1 and about 2.5 moles/mole beig particularly preferred.

The reaction medium is a mixture of water and an organic solvent, which is inert in the reaction. In this instance, "inert in the reaction" means that it does not chemically react with the catalyst produced. This excludes substitution of a co-ordinatively bound ligand which, as is well known to those skilled in the art, is extremely facile with this type of molecule. Thus, the organic solvent can be chosen from a lower di-alkyl ketone, such as acetone and butan-2-one, a lower alcohol, which also covers glycols, such as methanol, ethanol, propanol, propan-2-ol, butanol, 2-methyl-propan-2-ol and ethan-1,2-diol, an ether, such as tetrahydrofuran and dioxane, an organic nitrile, such as acetonitrile or a lower di-alkyl amide, such as dimethylformamide. An especially preferred organic solvent is acetone.

The reaction is carried out between 0° C. and the reflux temperature of the medium, with between 50° C. and 80° C. being the optical range. Below 0° C. the reaction is too slow to be of practical interest. The reaction time is typically between about 1 and about 5 hours, although the usual reaction time is about 3 hours. Whilst the catalysts can be prepared as described above, the use of an inert atmosphere, such as nitrogen, is preferred.

In this process, the catalyst is usually insoluble in the reaction mixture, and so can be obtained by simple conventional means, such as filtration. It might be found in some instances that a catalyst of the present invention is soluble in the reaction mixture, when addition of a miscible solvent, in which the catalyst is insoluble, would be advantageous. The solvent should not react with the catalyst so formed, a preferred example being di-isopropyl ether. After the filtration, the catalyst is usually washed with an organic solvent in which it is insoluble, di-ethyl ether being preferred, followed by drying at room temperature.

A further method, which forms another inventive feature of the present invention, is that the rhodium trichloride can be reacted with a hydrazine, in the absence of any added triphenyl phosphine. The hydrazine, which is preferably hydrazine itself, in the form of its trihydrate, is present in excess, typically of the order of 10 moles/mole of rhodium present. As for the previous method of preparation, the reaction medium is water plus an organic solvent, which can be chosen from one of the following: a lower di-alkyl ketone; a lower alcohol; an ether; an organic nitrile; or a lower di-alkyl amide, as was discussed previously. The preferred solvent is acetone.

Again, the optimal range is from 50° C. to 80° C., and the time between about 1 and about 5 hours, with about 3 hours being preferred. The novel compounds can be obtained in a manner similar to those described before, such as filtration in the event that the compound is insoluble in the reaction mixture, or by addition of an organic solvent, in which the catalyst is insoluble, followed by filtration. Obviously, the solvent should not react with the product in any way, a preferred solvent being di-isopropyl ether.

It will be shown that these compounds require the presence of triphenyl phosphine in order to be catalysts in the hydrogenation reaction. This is more fully discussed in U.S. Pat. No. 4,500,458.

In order to prepare compounds for X-ray crystallographic analysis, it is necessary to have relatively large crystals. Further it is known that rhodium complexes are liable to react with oxygen, thus causing difficulties in the exact interpretation of the analytical data. Thus, a preferred method by which such novel compounds can be obtained by the preparative methods hereinabove described, is by the use of degassed solvents and an inert atmosphere, such as nitrogen. The isolation is carried out by slow cooling of the reaction mixture or by slow addition of a degassed non-solvent followed by cooling. A preferred treatment is to cool for between 2 and 12 hours, under a stirring of 30 to 120 rotations/minute. The compounds of the present invention are then filtered and dried under an inert atmosphere.

For the practical use of these novel catalysts, these conditions are not necessary, since the small amount of oxygen which might be absorbed during manipulation, will have negligible influence on the activity or performance of the catalysts.

Naturally, any amount of rhodium eventually remaining in the mother liquors of the preparation of any of the above catalysts can easily be recovered, practically without loss, by conventional methods and recycled.

As has already been mentioned, certain of the compounds of the present invention have been analysed by X-ray crystallography, whilst others, for which this technique has not been possible, have been analysed by various other analytical methods.

Thus, the product obtained in Example 15A was shown to have the following structure by X-ray crystallography:

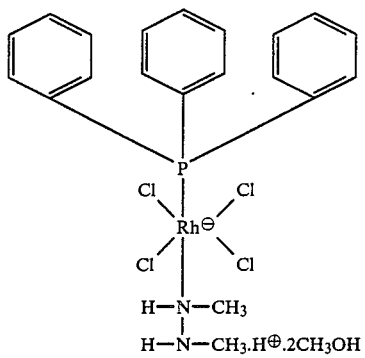

whilst that obtained in Example 16 was shown, by a combination of mass spectrometry, elemental analysis, infra-red absorption and nuclear magnetic resonance spectrometry to have the following structure:

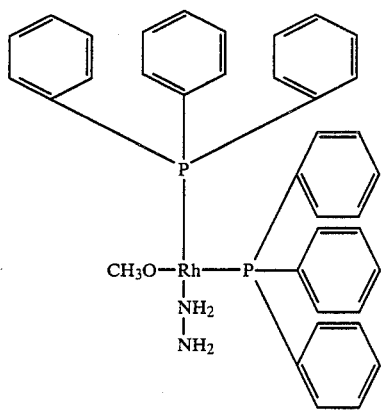

Divergence between the catalysts of the present invention and those of the prior art is easily provided by infra-red spectrometry also. The Wilkinson catalyst, tris(triphenylhosphine)chlororhodium (I), shows peaks at the following positions:
5.80(s); 6.00(s); 6.76(m); 7.00(m); 7.65(m); 8.45(m); 8.65(m); 8.95(m); 9.20(m); 9.73(ms); 10.20(s); 13.50(l, b); 14.40(l, b) microns
where
s, m, l stand for small, medium and large peaks, respectively, and b stands for broad.

The catalysts of the present invention have broad medium peaks at about 6.30 microns. An inspection of comparative spectra shows that this peak is not present in the Wilkinson catalyst.

From the various results obtained it was deduced that the catalysts had the general formula:

$(PPh_3)_a(R'_1R'_2N.NR'_3R'_4)_bRh_cX_d$ where X represents an anion, preferably chloro or methoxyl, Ph is phenyl and a, b, c and d are all integers, equal or greater than one. In the case of the compound obtained in Example 15A, there is also present a proton, so as to maintain the electro-neutrality of the molecule.

However, this postulated general formula has not yet been confirmed by X-ray crystallography for all of the prepared compounds, so one could eventually reach the conclusion that this general structure may not cover all of the compounds prepared according to the present invention. The present invention relates to the products obtained by the processes herein described and not to a particular nomenclature or a possible structure.

The following examples are given by way of illustration of the present invention, without in any way limiting the scope thereof.

EXAMPLE 1

Tris(triphenylphosphine)chlororhodium (I) (3.00 g; 3.24 mmoles) was added to hydrazine hydrate (0.48 ml; 9.88 mmoles) in 95% ethanol (60 ml). The mixture was stirred at room temperature (28° C.) for 90 minutes in an atmosphere of nitrogen, during which time the colour of the suspension changed from purple-red to orange. The solid was filtered, washed with di-isopropyl ether, and dried to yield 1.63 g. Concentration of the mother liquors under vacuum at low temperature provided a further 1.22 g. The infra-red spectrum showed a broad peak at 6.30 microns.

EXAMPLE 2

The conditions of Example 1 were repeated, except that the reaction mixture was refluxed for 25 minutes, instead of being stirred at room temperature. The yield of the orange first fraction was 1.40 g, with a further amount being obtained by concentration of the mother liquors. The infra-red spectrum showed a broad peak at 6.30 microns. Elemental analysis showed the product to contain 16.95% rhodium and 4.25% nitrogen.

Illustration of the application of the catalyst:

(A) Hydrogenation: 25 mg of the thus obtained catalyst in 20 ml of methanol was added to a stainless steel hydrogenation apparatus under magnetic stirring, containing 7.38 g of 6-methylene-5-hydroxytetracycline hydrochloride (MOT HCl) and 0.1 g of triphenylphosphine in 40 ml of methanol. After purging with nitrogen, hydrogen was added at a pressure of 8 kg/cm$^2$ and heated up to 89° C. After 5 h 30 m the comsumption dropped, and 1 hour later the reaction mixture was cooled down. The reaction mixture was filtered through a G4 glass-filter, then 3.3 g of p-toluenesulphonic acid was added to the filtrate and stirred. The α-6-deoxy-oxytetracycline p-toluenesulphonate thus formed was filtered, washed with acetone and dried. The product, which weighed 9.65 g, had the following analytical values: humidity 3.13% by the Karl Fischer method, yield 98.4% and purity 99.8% on anhydrous basis. No β-isomer or starting material were detectable by circular paper chromatography ("Schleicher & Schüll" paper No. 2045 B, 265 mm, ref. No. 381804; stationary phase: 100 ml of a solution of 0.1M citric acid and 40 ml of 0.2M anhydrous disodium phosphate were mixed to make a buffer with pH 3.5; mobile phase: nitromethane:chloroform:pyridine-20:10:3).

(B) 15 mg of the triphenylphosphine-hydrazinochlororhodium complex obtained above, was added in 20 ml of methanol to a stainless steel hydrogenator containing 10 g of 11a-chloro-6-deoxy-6-demethyl-6-methylene-5-hydroxytetracycline p-toluenesulphonate and 4 g of triphenylphosphine in 40 ml of methanol. The hydrogenate was flushed with nitrogen and filled with hydrogen to a pressure of 9.2 kg/cm$^2$ at 88° C. After 9 h 30 m, it was cooled down and the reaction mixture was filtered. 3.3 g of p-toluenesulphonic acid was added and stirred for 2 hours. The crystals thus formed were filtered and washed. The α-6-deoxy-oxytetracycline p-toluenesulphonate thus obtained weighed 8.0 g. Yield 84.2%. No β-epimer or starting material were detectable in the product by circular paper chromatography.

EXAMPLE 3

The conditions of Example 1 were repeated, using methanol as the solvent and a reaction time of 20 minutes. The filtered solid was light brown, with the first fraction weighing 1.40 g. Addition of di-isopropyl ether and concentration yielded two further fractions totalling 1.59 g. A broad peak at 6.30 microns was present in the infra-red spectrum. Elemental analysis showed the first fraction to contain 15.53% rhodium and 2.52% nitrogen.

A reaction mixture similarly prepared (0.5 ml) was treated with 11a-chloro-6-deoxy-6-demethyl-6-methylene-5-hydroxytetracycline p-toluenesulphonate (10.00 g; 15.4 mmoles) and triphenylphosphine (4.00 g; 15.25 mmoles), and then the hydrogenation was carried out at about 88° C. for 6 h 30 m. Addition of p-toluenesulphonic acid to the cooled reaction mixture caused crystallisation of doxycycline p-toluenesulphonate in a 82.7% weight/weight yield. The specific rotation in methanol containing 1% hydrochloric acid was −77.5°.

EXAMPLE 4

The conditions of Example 1 were repeated, using propan-2-ol as the solvent. In this case, the mixture was stirred for 45 minutes, before the orange product was filtered off. The yield of the first fraction was 64% weight/weight, with a further 30% weight/weight obtained by adding di-isopropyl ether, concentrating and filtering. The infra-red spectrum showed the presence of a broad peak at 6.30 microns.

EXAMPLE 5

The use of n-butanol with the conditions of Example 1, and a reaction time of 20 minutes, gave an orange product weighing 1.43 g. A second fraction was obtained in the normal fashion. The elemental analysis showed a rhodium content of 18.32%.

EXAMPLE 6

A mixture of tris(triphenylphosphine)chlororhodium (I) (1.00 g; 1.08 mmoles) and hydrazine hydrate (2.50 ml; 51.4 mmoles) in n-butanol (40 ml) was heated for 25 minutes at 90° C. Addition of di-isopropyl ether to the cooled reaction mixture gave 0.25 g of a yellow solid. Further fractions can be obtained by addition of more di-isopropyl ether.

EXAMPLE 7

Tris(triphenylphosphine)chlororhodium (I) (1.00 g; 1.08 mmoles) and hydrazine hydrate (0.16 ml; 3.29 mmoles) were refluxed together in ethanol (20 ml) for 20 minutes. The colour changed from red to yellow. At this point, triphenylphosphine (3.00 g; 11.44 mmoles) was added and the reflux continued for a further 20 minutes. After cooling to room temperature, the brown product was filtered off. The infra-red spectrum of this product showed a broad band at 6.30 microns.

EXAMPLE 8

Phenylhydrazine (0.32 ml; 3.25 mmoles) was heated with tris(triphenylphosphine)chlororhodium (I) (1.00 g; 1.08 mmoles) in acetonitrile (20 ml) at 65° C. for 25 minutes in a nitrogen atmosphere. The solution was cooled, diluted with di-isopropyl ether and the beige solid collected by filtration. The yield was 25% weight/weight, with the mother liquors containing further product. Again the infra-red spectrum had a broad peak at 6.30 microns.

EXAMPLE 9

Rhodium trichloride trihydrate (1.00 g; 3.80 mmoles) was dissolved by heating in water (5.0 ml) at 70° C. for 1 hour. Under a nitrogen atmosphere, a solution of triphenylphosphine (1.95 g; 7.43 mmoles) in acetone (25.0 ml) was added over a period of 20 minutes. After stirring for a further 10 minutes, hydrazine hydrate (1.90 ml; 39.09 mmoles) was added and the mixture refluxed for 3 hours, then stirred at 45° C. for 1 hour. The crystalline solid was filtered off, washed with a little acetone and finally di-ethyl ether, to yield 1.05 g of an orange solid. The infra-red spectrum exhibited a broad peak at 6.30 microns, and the the elemental analysis showed the presence of 12.43% rhodium and 2.61% nitrogen.

EXAMPLE 10

Rhodium trichloride trihydrate (0.50 g; 1.90 mmoles) was dissolved in water (2.5 ml) by heating at 70° C. for 1 hour. Then a solution of triphenylphosphine (0.73 g; 2.78 mmoles) in acetone (12.5 ml) was added over 20 minutes, under an atmosphere of nitrogen. The mixture was stirred for 10 minutes, after which hydrazine hydrate (0.95 ml; 19.55 mmoles) was added. The mixture was refluxed for 3 hours and then stirred at 45° C. for 1 hour. The yellow product was collected by filtration, washed with a small amount of acetone and then with di-ethyl ether. The yield was 58%.

EXAMPLE 11

Example 9 was repeated, substituting phenylhydrazine (3.85 ml; 39.1 moles) for the hydrazine hydrate. The yellowish orange product weighed 2.10 g, and the infra-red spectrum exhibited a broad peak at 6.30 microns.

EXAMPLE 12

Rhodium trichloride trihydrate (0.50 g; 1.90 mmoles) was dissolved in water (2.5 ml) by heating at 70° C. for 1 hour, after which a solution of triphenylphosphine (0.98 g; 3.74 mmoles) in butan-2-one (12.5 ml) was added over 20 minutes. The mixture was stirred for 10 minutes in an atmosphere of nitrogen. Benzenesulphonylhydrazine (3.37 g; 19.57 mmoles) was added, and the mixture stirred at 67° C. for 3 hours and at 45° C. for 1 hour, under a nitrogen atmosphere. Filtration of the cooled reaction mixture yielded 0.93 g of an orange product. The infra-red spectrum exhibited a peak at 6.30 microns.

EXAMPLE 13

Rhodium trichloride trihydrate (0.50 g; 1.90 mmoles) was dissolved in water (2.5 ml) by heating at 70° C. for 1 hour. A solution of triphenylphosphine (0.975 g; 3.72 mmoles) and hydrazine di-hydrochloride (2.05 g; 19.53 mmoles) in acetone (12.5 ml) was added during 20 minutes, under an atmosphere of nitrogen. After stirring for 10 minutes, the mixture was refluxed for 3 hours. On cooling, a cream coloured product crystallised. After filtration, washing with a small amount of acetone and finally with di-ethyl ether, a yield of 1.05 g was obtained.

EXAMPLE 14

Rhodium trichloride trihydrate (0.50 g; 1.90 mmoles) was dissolved in water (2.5 ml) by heating at 70° C. for 1 hour. A solution of triphenylphosphine (0.975 g; 3.72 mmoles) in methanol (12.5 ml) was added under a nitrogen atmosphere during 20 minutes. After 10 minutes stirring, hydrazine hydrate (0.95 ml; 19.55 mmoles) was added, and the mixture refluxed under nitrogen for 3 hours. On cooling, a solid crystallised. It was collected by filtration, washed with a small amount of methanol and finally with di-ethyl ether. The orange solid weighed 0.57 g.

EXAMPLE 15

A. Catalyst: Tris(triphenylphosphine)chlororhodium (I) (0.5 g; 0.54 mmoles) was refluxed under a nitrogen atmosphere with N,N'-dimethylhydrazine dihydrochloride (0.215 g; 1.62 mmoles) in dry, degassed methanol (30 ml) for 90 minutes. The colour of the reaction mixture changed from purple-red to orange during this time. On cooling, a product crystallised which was filtered, washed and dried. A second fraction could be obtained by addition of di-isopropyl ether to the mother liquors.

B. Hydrogenation: The catalyst prepared as above (25 g) was used in a repetition of Example 2A. The yield of α-6-deoxy-oxytetracycline p-toluenesulphonate was 8.78 g, which was shown to be 99.4% pure by hplc, thus corresponding to a yield of 91.8%.

EXAMPLE 16

Tris(triphenylphosphine)chlororhodium (I) (0.48 g; 0.52 mmoles) was refluxed under nitrogen for 90 minutes with hydrazine hydrate (76 μl; 1.56 mmoles) in dry, degassed methanol (20 ml). The yellow orange solution was cooled to yield a yellow solid. Analysis by mass spectrometry, elemental analysis, infra-red spectroscopy and nuclear magnetic resonance spectrometry showed the structure to be bis(triphenylphosphine)hydrazinomethoxylrhodium (I).

We claim:

1. A process for the preparation of a homogeneous stereospecific rhodium complex hydrogenation catalyst, of a uniform and well defined composition, containing rhodium, a hydrazine and triphenylphosphine, as well as an anion, comprising reacting a rhodium salt with a hydrazine, or a salt thereof, having the formula $R'_1R'_2N.NR'_3R'_4$, wherein $R'_1$, $R'_2$, $R'_3$ and $R'_4$ are lower alkyl groups or hydrogen, in the presence of triphenylphosphine, or by reacting a complex of rhodium and triphenylphosphine with said hydrazine or salt thereof, eventually in the presence of an excess of triphenylphosphine, characterized by the fact that the reaction is carried out in a mixture of a degassed organic solvent, miscible in the reaction, and eventually water, at a temperature between 0° C. and the reflux temperature of the reaction medium for between 20 minutes and 5 hours, under an inert atmosphere, and the isolation of the catalyst is carried out by cooling when the complex so formed is little soluble in the cold reaction mixture, or by slow addition of a degassed inert non-solvent and by cooling when the complex prepared is soluble in the reaction mixture, followed by filtration and drying under an inert atmosphere.

2. A process according to claim 1, wherein the rhodium salt is rhodium trichloride trihydrate.

3. A process according to claim 1, wherein the reaction is carried out in the presence of excess triphenyl phosphine.

4. A process according to claim 1, wherein the hydrazine is hydrazine itself, N,N-dimethylhydrazine, N,N'-dimethylhydrazine, tetramethylhydrazine, or a salt thereof.

5. A process according to claim 1, wherein the hydrazine is present in a molar excess with respect to the moles of rhodium.

6. A process according to claim 1, wherein the organic solvent is a lower di-alkyl ketone, a lower alcohol, an ether, an organic nitrile or a lower di-alkyl amide.

7. A process according to claim 1, wherein the lower di-alkyl ketone is acetone or butan-2-one, the lower alcohol is methanol, ethanol, propanol or butanol, the ether is tetrahydrofuran or dioxane, the organic nitrile is acetonitrile and the lower dialkyl amide is dimethylformamide.

8. A process according to claim 1, wherein the anion, forming part of the complex, is a halogen or methoxide.

9. A process according to claim 1, wherein the cooling or the addition of the non-solvent is carried out between 2 to 12 hours, under a stirring of between 30 and 120 rotations/minute.

10. A process according to claim 1, wherein the degassed solvent is methanol and the inert atmosphere is nitrogen.

11. A process according to claim 1, wherein the rhodium complex is prepared by reacting 1 mole of tris(triphenylphosphine)rhodium chloride and 3 moles of N,N'-dimethylhydrazine dihydrochloride, or 1 mole of rhodium trichloride, 4 moles of triphenylphosphine and 3 moles of N,N'-dimethylhydrazine dihydrochloride, in a degassed solvent, under an atmosphere of nitrogen, at reflux temperature, and slowly cooling, after complete reaction, for 6 hours at 0° C. under slow stirring, followed by filtration and drying under an atmosphere of nitrogen, to furnish a homogeneous stereospecific rhodium complex hydrogenation catalyst of the formula:

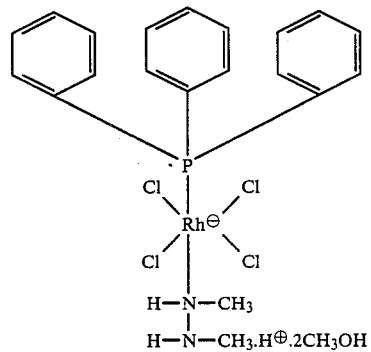

12. A process according to claim 1 wherein the rhodium complex is prepared by reacting 1 mole of tris(triphenylphosphosphine)rhodium chloride and 3.05 moles of hydrazine hydrate in a degassed solvent, under an atmosphere of nitrogen, at room temperature and, after complete reaction, slowly cooling the reaction mixture, for 10 hours under slow stirring to 0° C, to furnish a homogeneous stereospecific rhodium complex hydrogenation catalyst of the formula:

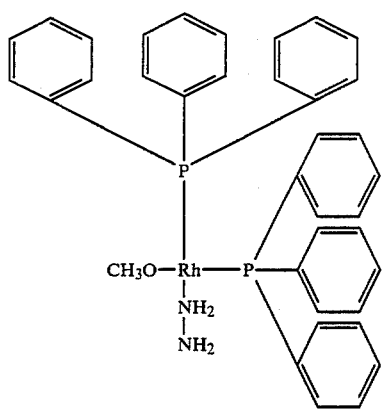
13. The compound [P(C$_6$H$_5$)$_3$.(CH$_3$NH.NHCH$_3$)RhCl$_4$]$^\ominus$.H$^\oplus$.2CH$_3$OH.
14. The compound bis(triphenylphosphine)hydrazinomethoxyrhodium (I).
* * * * *